(12) United States Patent
Doyle et al.

(10) Patent No.: US 9,034,616 B2
(45) Date of Patent: May 19, 2015

(54) **BUTANAL PRODUCTION USING ENGINEERED *STREPTOMYCES COELICOLOR***

(75) Inventors: Robert Doyle, Syracuse, NY (US); Joshua Lensbouer, Fayetteville, NY (US); Anthony Vortherms, Fayetteville, NY (US)

(73) Assignee: Syracuse University, Syracuse, NY (US)

( * ) Notice: Subject to any disclaimer, the term of this patent is extended or adjusted under 35 U.S.C. 154(b) by 279 days.

(21) Appl. No.: 12/754,792

(22) Filed: Apr. 6, 2010

(65) Prior Publication Data

US 2010/0255552 A1    Oct. 7, 2010

Related U.S. Application Data

(60) Provisional application No. 61/166,938, filed on Apr. 6, 2009.

(51) Int. Cl.
| | |
|---|---|
| *C12P 7/16* | (2006.01) |
| *C12N 9/00* | (2006.01) |
| *C12N 1/20* | (2006.01) |
| *C07H 21/04* | (2006.01) |
| *C12N 1/22* | (2006.01) |
| *C12P 7/24* | (2006.01) |

(52) U.S. Cl.
CPC .. *C12N 1/22* (2013.01); *C12N 9/93* (2013.01); *C12P 7/16* (2013.01); *C12P 7/24* (2013.01); *Y02E 50/10* (2013.01)

(58) Field of Classification Search
None
See application file for complete search history.

(56) References Cited

PUBLICATIONS

Inui et al. Appl Microbiol Biotechnol. Jan. 2008;77(6):1305-16. Epub Dec. 1, 2007.*
van Wezel et al. Appl Environ Microbiol. Aug. 2006;72(8):5283-8.*
Ratnatilleke et al. J Biol Chem. Oct. 29, 1999;274(44):31679-85.*
Tabata et al. Biotechnol Lett. Oct. 2004;26(19):1487-91.*

* cited by examiner

*Primary Examiner* — Christian Fronda
(74) *Attorney, Agent, or Firm* — David L. Nocilly; Bond Schoeneck & King, PLLC

(57) ABSTRACT

A method of producing butanal by optimizing the growth of *Streptomyces* using cellulose as food source, overexpressing a key 'gate' enzyme in butyric acid/butyraldehyde production, and knocking out the isobutyryl-CoA synthase gene to shunt the pathway. Optionally, the produced butanal can be isolated and converted into butanol.

19 Claims, 5 Drawing Sheets

BUTANAL PRODUCTION USING ENGINEERED *STREPTOMYCES COELICOLOR*

CROSS-REFERENCE TO RELATED APPLICATION

The present application claims priority to U.S. Provisional Application No. 61/166,938, filed Apr. 6, 2009, which is incorporated herein by reference in its entirety.

BACKGROUND OF THE INVENTION

1. Field of the Invention

The present invention relates to method for producing butanal (butyraldehyde) and, more particular, to a method for producing butanal using genetically engineered *Streptomyces coelicolor*.

2. Description of the Related Art

Batch culturing and fermentation processes using microorganisms provide an efficient and cost-effective means of producing biochemicals and bioproducts. Using abundant non-anthropogenic feedstock as the starting material for producing these biomaterials is the goal of many scientists. It is estimated that over one billion dry tons of non-anthropogenic feedstock are available for use each year in the United States, almost half of which is available for under $40 a dry/ton.

As crude oil prices have risen, biochemicals and bioproducts have become increasingly attractive to the chemical and manufacturing world. Biochemicals and bioproducts such as butyraldehyde have many characteristics that make them better than most oil-based products, including the following: (a) lower greenhouse gas emissions from its production; (b) lower production costs due to starting materials; (c) fewer renewable starting materials are typically used; and (d) all the same physical properties as petroleum-based butyraldehyde. Butyraldehyde is used industrial applications in solvents and intermediates. The primary use for n-butyraldehyde, an intermediate formed using the subject technology, is as a chemical intermediate in producing other chemical commodities such as 2-Ethylhexanol (2-EH). 2-EH is widely used in plasticizers, coatings and adhesives. Other products requiring n-butyraldehyde include trimethylolpropane (TMP), n-butyric acid, polyvinyl butyral (PVB), n-butanol, and methyl amyl ketone. Smaller applications include intermediates for producing pharmaceuticals, crop protection agents, pesticides, synthetic resins, antioxidants, vulcanization accelerators, tanning auxiliaries, perfumery synthetics, and flavors.

With successful overproduction of butyraldehyde, a shift in use from chemical intermediates to conversion of butanol is predicted. Butanol or butyl alcohol (sometimes also called biobutanol when produced biologically), is a primary alcohol with a 4 carbon structure and the molecular formula of $C_4H_9OH$. Butanol is used as a solvent, as an intermediate in chemical synthesis, and as a fuel. Currently, n-butanol is being considered as an additive to gasoline. The current global market is about 350 million gallons per year with the U.S. market accounting for about 220 million gallons per year. Production of butanol for a gasoline additive could produce a demand of 72 million gallons a day in the United States.

Butyraldehyde is traditionally made by the hydroformulation of propylene. Cobalt catalysts were the original catalysts used, but newer rhodium catalysts are now being employed. Butyraldehyde can also be produced by the oxidation of butanol or hydrogenation of crotonyl. Butyraldehyde has never been successfully produced by an organism on an industrial scale.

Acetone-butanol-ethanol (ABE) fermentation with *Clostridium acetobutylicum* was once a widely used industrial fermentation process providing acetone, which was used to produce cordite. However, production of acetone from propylene has contributed to the downward spiral of ABE fermentation. ABE fermentation for production of butanol has gained interest since the 1980's as a use for gasoline additives, but limitations still prevent industrial scale production. Limitations associated with industrial scale production include: (a) low butanol yield from glucose (15-25%); (b) low reactor productivity (0.5 g/L·h); (c) low final concentrations of less than 15 g/L; and (d) expensive purification. As a result, ABE fermentation is not cost competitive with petroleum-based butanol production. Accordingly, there is a continued need for an inexpensive and effective method of producing both butanol and butanol precursors such as butyraldehyde and butyric acid.

BRIEF SUMMARY OF THE INVENTION

The present invention provides the production of butanal using *Streptomyces coelicolor* in three stages. Each stage describes a particular issue involved in successfully producing butanal. Some of the issues are overcome with the choice of the organism itself (see stage 1), but others require genetic manipulation of the organism and a need to overcome the toxicity of the target product, which typically becomes toxic at levels starting between 1.5-3%. FIG. 1 describes the course of action with each of the four major stages indicted by numbers 1 through 4. The process is designed to use *Streptomyces coelicolor*'s innate ability to digest cellulose. Also critical is the basic machinery already in place that, suitably overexpressed and controlled, can be transformed to produce butyraldehyde or butyric acid.

Once the organism produces the butyraldehyde or butyric acid, facile isolation and chemical conversion to butanol can be used to produce the final product. A key point in stopping biosynthesis pre-butanol is the fact that the toxicity of butanol is overcome since butyraldehyde and butyric acid are naturally produced in *Streptomyces coelicolor* and are far less toxic to the organism than butanol. Finally, it should be noted that the organism, the necessary vectors and the desired acetoacetyl-CoA synthase gene are all already located with IntelliSyn™ or can be obtained from commercial sources with no inhibitory ties.

Instead of producing butyraldehyde directly from anthropogenic feedstock, which is inherently cost fluctuating and uneconomical, a bacterium that turns non-anthropogenic feedstock (e.g. cellulose) into butyraldehyde provides a mechanism around the hurdles of fermentation. Many ethanol plants use anthropogenic feedstock as a source of starting material. However, anthropogenic feedstock is contentious in that ethanol production competes with feeding people, which also causes the price of starting material to fluctuate with crop production. A solution to overcome demand is to use materials that are waste products or have no market. Agricultural waste provides an ideal source of starting material, but must first be converted to fermentable sugars. The conversion of agricultural waste to fermentable sugars adds additional cost to the fermentation process, which makes ethanol production from non-anthropogenic feedstock non-economical compared to petroleum products. A solution to overcome the cost of conversion is to use a bacterium that converts cellulose into usable sugars naturally. Using a bacterium (e.g. *Streptomyces*) to convert cellulose to glucose would overcome the expensive cost of enzymatically converting cellulose to glucose. However, if the bacterium does not produce the end product, i.e. butyraldehyde, than an additional organism is necessary to convert the glucose into the desired end product.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
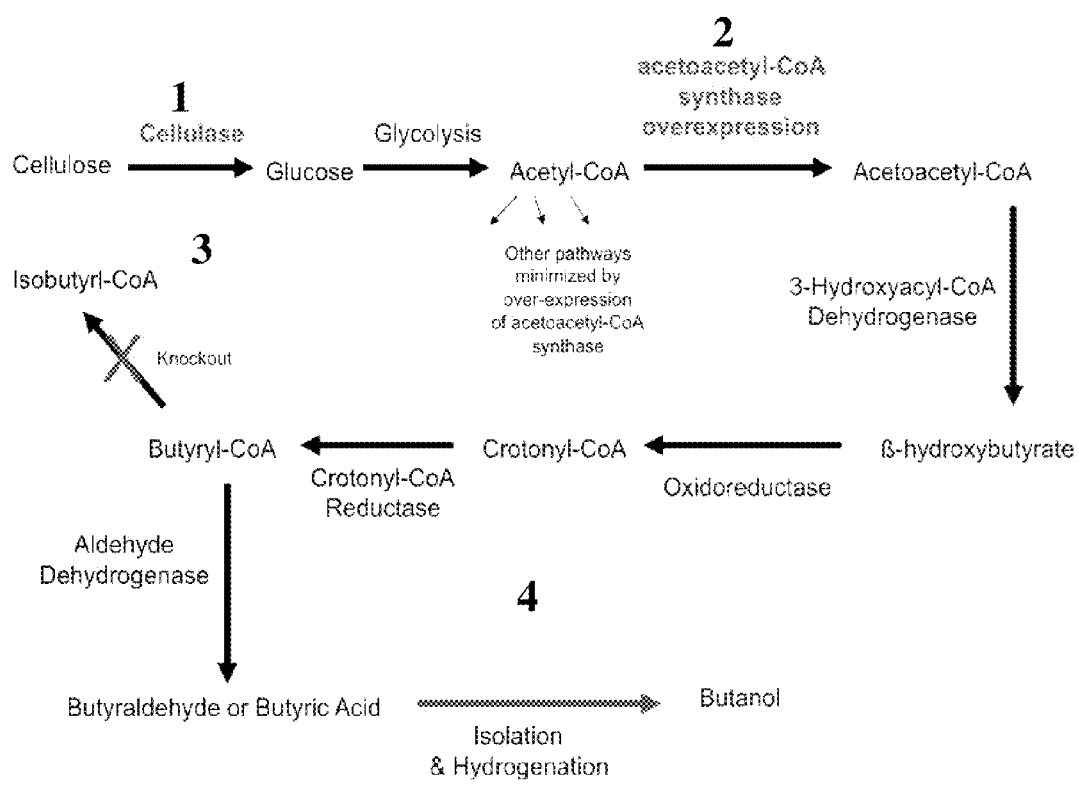
FIG. 1 is a schematics of the combined chemical and biochemical route to butanal production in *Streptomyces coelicolor*.

Referring now to the drawings, wherein like reference numerals refer to like parts throughout, there is seen in FIG. 1 a course of action according to the present invention with each of the four major stages numbered 1 through 4.

Stage 1. Optimizing Growth of *S. Coelicolor* Using Cellulose as Food Source.

Utilization of a cheap and readily available energy source is a primary goal and objective of any product production. A vast amount of time and energy is spent building or finding an organism capable of processing key raw materials. The present organism is a strain of *Streptomyces coelicolor* A3(2), which is a soil-dwelling organism that can produce antibiotics, access iron-citrate, and in general conduct a wide array of complex reactions. Of key interest here is the fact that *S. coelicolor* can digest chitin, lectin, and cellulose. This means that *S. coelicolor* can be grown in cheap, minimal media containing only basic salts supplemented in cellulose as the only carbon/energy source. It has previously been demonstrated that the organism will grow in minimal media with citrate as the only carbon/energy source. See, e.g., R. P. Doyle, et al., 2008, Functional Characterization and Metal Ion Specificity of the Metal-Citrate Complex Transporter From *Streptomyces coelicolor*, J. BACTERIOL. 190(16):5616-23. In a preferred embodiment, the *Streptomyces* strain is batch cultured at 28-32° C.

Other *Streptomyces* species which are or might be suitable for the production of butyraldehyde include, but are not limited to, *S. achromogenes, S. albus, S. ambofaciens, S. aureomonopodiales, S. aureofaciens, S. avermitilis, S. bikiniensis, S. caespitosus, S. chusanensis, S. clavuligerus, S. coelicolor, S. diastaticus, S. exfoliatus, S. faecalis, S. faecium, S. felleus, S. ferralitis, S. fimbriatus, S. filamentosus, S. fradiae, S. fulvissimus, S. griseoruber, S. griseoviridis, S. griseus, S. hygroscopicus, S. iysosuperficus, S. lavendulae, S. lividans, S. lusitanus, S. niveus, S. nodosus, S. noursei, S. novocastria, S. olivochromogenes, S. phaeochromogenes, S. pulveraceus, S. scabies, S. somaliensis, S. stanford, S. tendae, S. thermodiastaticus, S. thermoviolaceus, S. toxytricini, S. tsukubaensis, S. tubercidicus, S. venezuelae, S. violaceoruber,* and *S. violochromogenes*. Genetic modification of the *Streptomyces* includes, but is not limited to, overexpressing acetyl-CoA transferase to make acetoacetyl-CoA, knocking out butyryl-CoA isomerase, and overexpressing butyryl-CoA dehydrogenase. Additional genetic modifications could include overexpressing cellulases for increased biomass conversion to butyraldehyde.

Stage 2. Overexpression of Key 'Gate' Enzyme in Butyric Acid/Butyraldehyde Production.

Figure 2:
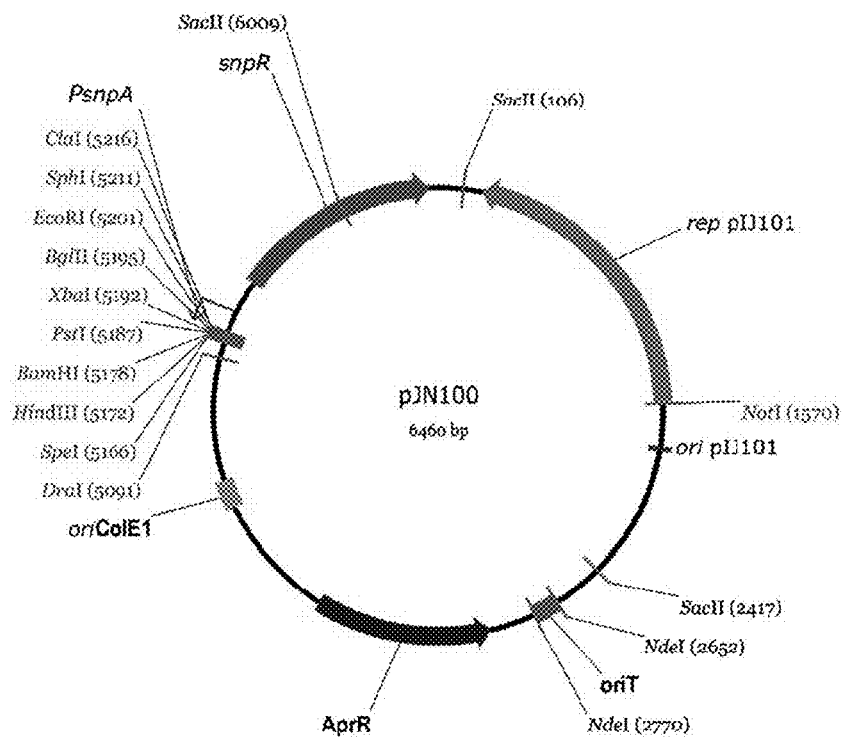
FIG. 2 is a schematic of the *E. coli/Streptomyces* shuttle vector pJN100 used to insert the acetoacetyl CoA synthase gene into *S. coelicolor*.
Figure 3:
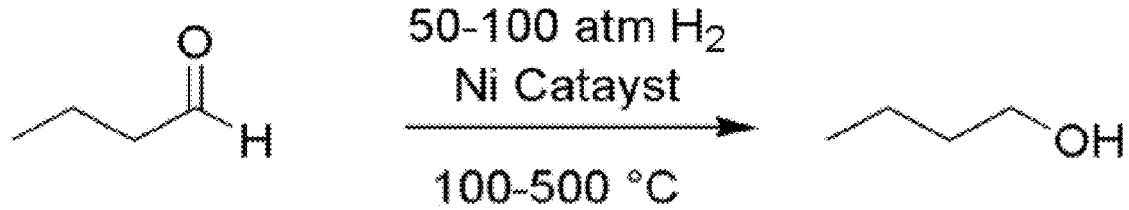
FIG. 3 is the chemical reduction of butanal over a nickel catalyst.

Stage 2 involves overexpression of the 'gate' enzyme of the pathway. By overexpressing acetoacetyl-CoA synthase the system is forced to push the pathway along to a point at which the pathway will be controllably stopped and 'shunted' towards the desired product. The pJN100 shuttle vector, shown in FIG. 2, is used to achieve overexpression of acetoacetyl-CoA synthase. This vector enables the user to clone and prepare the gene in *E. coli* for insertion into *S. coelicolor*, which greatly speeds up the process. The vector can also provide for antibiotic resistance. For example, in one embodiment, the vector provides for actimycin resistance, which, when coupled with stage 3, provides dual antibiotic resistance. The gene for acetoactyl-CoA can be created or cloned using any method known to those skilled in the art. In a preferred embodiment, a gene for acetoacetyl-CoA synthase is built by Integrated DNA Technologies™ in Indiana, USA. The right to use the gene without interference is retained upon receipt.

Stage 3. Knockout of Isobutyryl-CoA Synthase Gene to Shunt Pathway.

As seen in FIG. 2, *E. coli/Streptomyces* shuttle vector pJN100 is used to insert the acetoacetyl-CoA synthase gene into *S. coelicolor*. Removal of the isobutryrl-coenzyme A ("isobutyryl-CoA") synthase gene will be achieved using the TargeTron® Gene Knockout System, which allows for the specific and rapid disruption of bacterial genes by insertion of Group II Introns. This system will allow for both the knockout of the isobutyryl-CoA synthase gene and also provide bacterial resistance to kanamycin, allowing for screening of the desired mutant and additional protection against contamination. By removing isobutyryl-CoA synthase the biosynthetic pathway will 'build-up' butyrl-CoA which will then be 'shunted' into the production of either/both butyraldehyde (also known as butanal) or butyric acid (also known as butanoic acid).

Stage 4. Isolation of Butyraldehyde/Butyric Acid and Optional Conversion into Butanol.

The production of butyraldehyde/butyric acid can be achieved and monitored by any means known to those skilled in the art. In a preferred embodiment, the production of butyraldehyde/butyric acid is monitored by gas chromatography-mass spectrometry ("GC-MS"). GC-MS will be able to confirm the concentration of the compounds in the broth and confirm the molecular weight of the compounds being produced.

Figure 4:
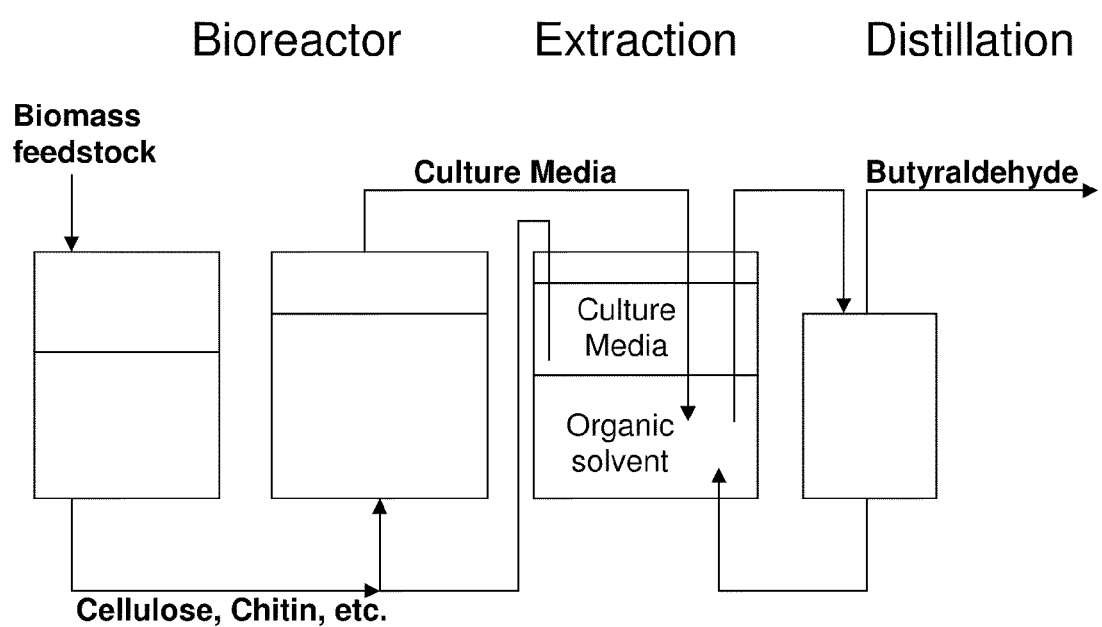
FIG. 4 is a schematic representation of butyraldehyde batch-culturing according to one embodiment of the present invention.
Figure 5:
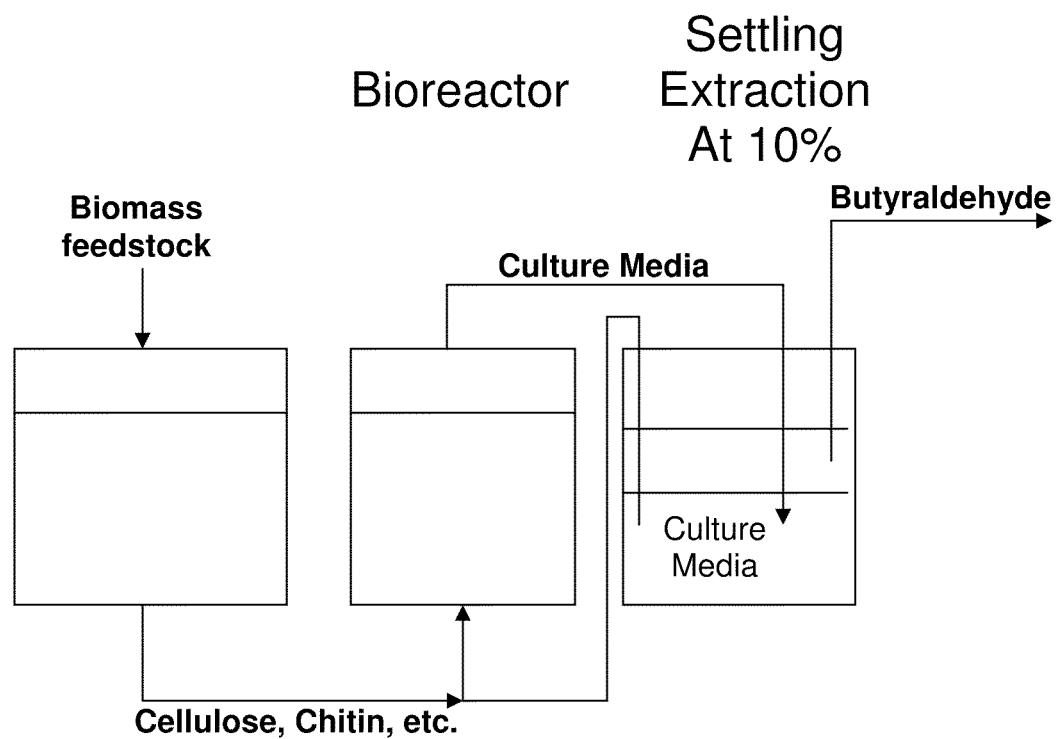
FIG. 5 is a schematic representation of butyraldehyde batch-culturing according to a second embodiment of the present invention.
Figure 6:
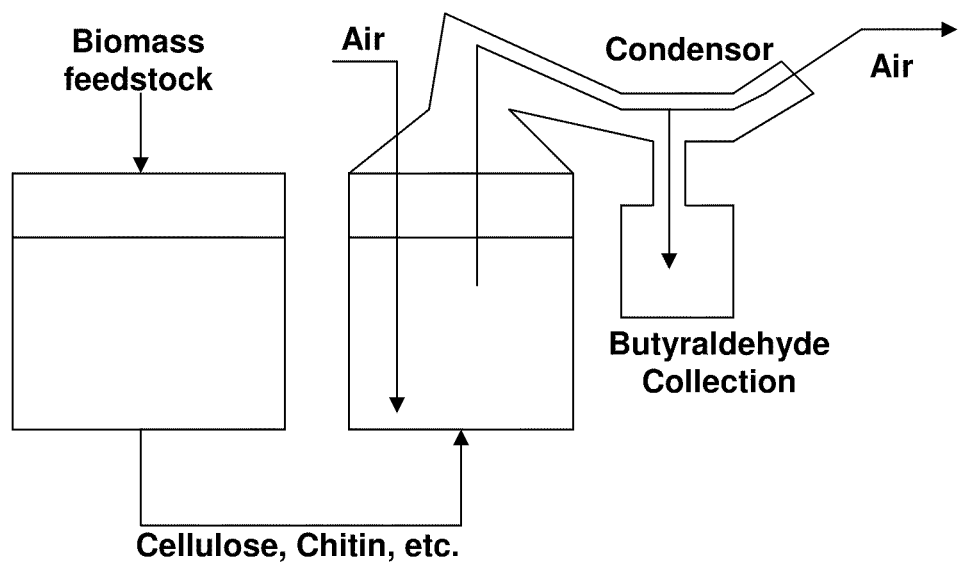
FIG. 6 is a schematic representation of butyraldehyde batch-culturing according to a third embodiment of the present invention.

Isolation of butyraldehyde/butyric acid from the broth via can be achieved by any means of chemical purification, distillation, fractionation, or isolation known in the art, as shown in FIGS. 4-6. FIG. 4 is a schematic representation of butyraldehyde batch-culturing according to one embodiment of the present invention in which feedstock is fed into the bioreactor containing bacteria and converted to butyraldehyde. Culture media is pumped out into a separation chamber containing a butyraldehyde miscible solvent, but not a water miscible solvent. The culture media would be pumped in at the bottom of the tank so that the culture media would have to travel through the organic solvent. Once the culture media reaches the top and creates a biphasic layer, the culture media absent of the butyraldehyde could be pumped back into the bioreactor. The butyraldehyde miscible solvent is pumped into a distillation chamber and butyraldehyde is separated.

FIG. 5 is a schematic representation of butyraldehyde batch-culturing in which feedstock is fed into the bioreactor containing bacteria and converted into butyraldehyde. The culture media is pumped out into a settling chamber. Once butyraldehyde reaches 10% v/v of the culture, a biphasic layer occurs. The top layer is butyraldehyde with the bottom layer being culture media. The culture media can be pumped into a settling tank and the biphasic layer can be allowed to form. The butyraldehyde can be pumped off the top layer and purified, the culture media on the bottom can be pumped back into the bioreactor.

FIG. 6 is yet another schematic representation of butyraldehyde batch-culturing in which feedstock is fed into the bioreactor containing bacteria and converted into butyraldehyde. Air is pumped into the bioreactor, which causes the butyraldehyde to volatize into the air and both leave the culture media. The air containing the butyraldehyde hits a condenser and reenters the liquid state. A sloped funnel guides the butyraldehyde into a collection chamber and the air continues back into the ambient air.

In a preferred embodiment, butyraldehyde and/or butyric acid are isolated by fractional distillation. Butyraldehyde and butyric acid have distinct boiling points or 74.8° C. and 163.5° C., respectively. Before distillation the butyraldehyde/butyric acid can be extracted from the broth with octanol or a similar organic solvent. This concentrates the products and separates out aqueous impurities. The compounds can also be isolated from the broth by means of precipitation. The isolated butyraldehyde/butyric acid is characterized by boiling point, GC-MS, elemental analysis, $^1$H and/or $^{13}$C NMR.

Once produced, the isolated butyraldehyde/butyric acid can be used for any downstream use, product, or application. In a preferred embodiment, the butyraldehyde/butyric acid is converted to butanol using known conversion mechanisms.

Current methods of butanol production rely on biological reduction of produced butyraldehyde/butyric acid to butanol, which requires a second bacterial strain and a second fermentation process. Having a second fermentation step raises the cost of production by doubling the amount of water and fermentable sugars required. Butanol is also toxic to cells, which limits the total concentration of butanol that can be produced through fermentation. Chemically reducing the butyraldehyde/butyric acid to butanol can be achieved using well-established science, with only the cost of the catalyst and hydrogen source. The total yield of butanol reduction is high, and does not suffer from toxic concentration limitations.

Catalytic hydrogenation is the most common method for reducing chemical compounds on an industrial scale. This method requires addition of $H_2$ in the presence of a catalyst under high temperature and pressure. The catalyst may be a precious metal, which tends to give quicker reaction times, or a non-precious metal, while cheaper, yields a slower reaction. These nonprecious metal catalysts tend to be oxides like Zn, Mg, or Ni. Combining different metals together can help increase reaction time and yield (see, e.g., *Chem. Eng. J.,* 2008, Y. K. Park, et al. and *J. Phys. Chem.,* 1931, H. Adkins and L. W. Covert, hereby incorporated by reference).

Separating the target product butanol from the reaction mixture can be done by extraction, distillation (boiling point 117.73° C.), or precipitation. The butanol will be characterized by boiling point, GC-MS, elemental analysis, $^1$H and/or $^{13}$C NMR. Purity will be assayed to ASTM standards.

Although the present invention has been described in connection with a preferred embodiment, it should be understood that modifications, alterations, and additions can be made to the invention without departing from the scope of the invention as defined by the claims.

What is claimed is:

1. A genetically engineered microbe comprising:
   an inactivating mutation in a DNA molecule in the microbe, wherein the DNA molecule encodes a isobutyryl-CoA synthase; and
   an enzyme-encoding recombinant DNA molecule, wherein the enzyme-encoding recombinant DNA molecule encodes an acetoacetyl-CoA synthase.

2. The microbe of claim 1, wherein said microbe utilizes cellulose as an energy source.

3. The microbe of claim 1, wherein said microbe is a *Streptomyces* species.

4. The microbe of claim 1, wherein the acetoacetyl-CoA synthase gene originates from *Escherichia coli*.

5. A method of forming a genetically engineered microbe for producing butanal, comprising the steps of:
   introducing an inactivating mutation in a DNA molecule in the microbe, wherein the DNA molecule encodes a isobutyryl-CoA synthase; and
   introducing an enzyme-encoding recombinant DNA molecule, wherein the enzyme-encoding recombinant DNA molecule encodes an acetoacetyl-CoA synthase.

6. The method of claim 5, wherein said microbe is a *Streptomyces* species.

7. A method of producing butanal, comprising the steps:
   providing a genetically engineered microbe, wherein the microbe comprises an inactivating mutation in a DNA molecule in the microbe that encodes a isobutyryl-CoA synthase; and an enzyme-encoding recombinant DNA molecule in the microbe, wherein the enzyme-encoding recombinant DNA molecule encodes an acetoacetyl-CoA synthase;
   culturing the microbe in the presence of a carbon source; and
   isolating the butanal.

8. The method of claim 7, wherein said microbe is a *Streptomyces* species.

9. The method of claim 7, wherein the carbon source is cellulose.

10. The method of claim 7, further comprising the step: converting said butanal to butanol.

11. The method of claim 7, wherein the step of isolating said butanal comprises fractional distillation of the butanal.

12. The method of claim 7, wherein the step of isolating said butanal comprises precipitation of the butanal.

13. The method of claim 7, further comprising the step: extracting the butanal with an organic solvent.

14. The method of claim 10, wherein the step of converting the butanal to butanol comprises hydrogenation of the butanol precursor.

15. The method of claim 14, wherein the hydrogenation comprises a catalyst.

16. The method of claim 15, wherein the catalyst is a metal.

17. The method of claim 10, further comprising the step: isolating the butanol.

18. The method of claim 17, wherein the step of isolating the butanol comprises distillation of the butanol.

19. The method of claim 18, wherein the step of isolating the butanol comprises precipitation of the butanol.

* * * * *